(12) United States Patent
Pfeffinger et al.

(10) Patent No.: US 6,403,845 B1
(45) Date of Patent: Jun. 11, 2002

(54) PREPARATION OF PENTANEDIOLS FROM ALKOXYDIHYDROPYRANS

(76) Inventors: Joachim Pfeffinger, Bessemerstr.20, 67063 Ludwigshafen; Peter Wahl, Valentinianstr.8, 68526 Ladenburg; Jan Nouwen, Am Marktplatz 4, 64653 Lorsch; Karsten Eller, Bayernstr.45, 67061 Ludwigshafen; Arthur Höhn, Oberer Waldweg 17, 67281 Kirchheim; Jürgen Hunger, Kornackerstr.29a, 67067 Ludwigshafen, all of (DE)

( * ) Notice: Subject to any disclaimer, the term of this patent is extended or adjusted under 35 U.S.C. 154(b) by 80 days.

(21) Appl. No.: 09/625,487

(22) Filed: Jul. 25, 2000

(30) Foreign Application Priority Data

Jul. 29, 1999 (DE) .......................... 199 35 828

(51) Int. Cl.⁷ .............................. C07C 27/00
(52) U.S. Cl. ................... 568/865; 568/861; 568/866; 568/867
(58) Field of Search ................ 568/866, 861, 568/865, 867

(56) References Cited

U.S. PATENT DOCUMENTS 2,546,019 A * 3/1951 Smith .................. 260/635
6,069,281 A * 6/2000 Kropp et al. ............ 564/494

FOREIGN PATENT DOCUMENTS

| | | |
|---|---|---|
| DE | 1 003 704 | 3/1957 |
| DE | 44 14 274 | 10/1995 |
| GB | 653765 | 5/1951 |
| WO | WO 95/32171 | 11/1995 |

OTHER PUBLICATIONS

Ullmann's Encyclopedia of Industrial Chemistry, 5th Edition, vol. A1, pp. 307–315, Dec. 1984.

* cited by examiner

Primary Examiner—Sreeni Padmanabhan
Assistant Examiner—Elvis O. Price
(74) Attorney, Agent, or Firm—Keil & Weinkauf

(57) ABSTRACT

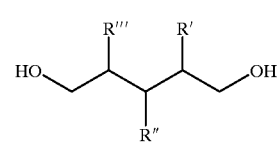

are prepared by single-stage reaction of alkoxydihydropyrans of the formula (II)

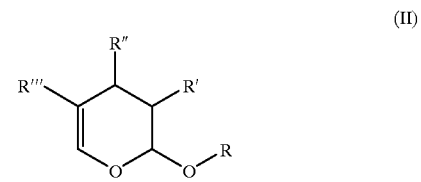

with water and hydrogen in the presence of a catalyst comprising oxides of nickel, zirconium and copper.

In the formulae (I) and (II),

R, R', R", R'" can be identical or different and are each hydrogen or a linear or branched saturated hydrocarbon radical having from 1 to 20 carbon atoms in which the hydrocarbon chain may contain O, S and N as heteroatoms and which may be monosubstituted or polysubstituted by hydroxy, thiol or amino groups or halogens.

8 Claims, No Drawings

PREPARATION OF PENTANEDIOLS FROM ALKOXYDIHYDROPYRANS

The present invention relates to a process for preparing 1,5-pentanediols by single-stage reaction of alkoxydihydropyrans with water and hydrogen in the presence of a catalyst and also to the use of the catalyst in this process.

1,5-pentanediol is an important intermediate for the production of polyesters, polyurethanes and heterocyclic compounds such as 1-methylpiperidine which are used as intermediates in the production of drugs and crop protection agents.

Pentanediol is produced industrially on a large scale, as described in Ullmann's Encyclopedia of Industrial Chemistry, 5th Edition, Vol. Al, p. 307, by catalytic hydrogenation of glutaric acid, which is obtained industrially as a coproduct in the production of adipic acid, or its esters. In the catalytic hydrogenation of adipic acid/glutaric acid mixtures, pentanediol is obtained in a proportion of only about 10 mol%. Furthermore, the isolation of very pure pentanediol from this mixture is difficult because of the very similar boiling points of pentanediol and hexanediol.

A further process for preparing pentanediol starts from glutaraldehyde which is obtained by acid hydrolysis of alkoxydihydropyrans. Processes for the hydrogenation of dialdehydes are described in DE-A 4 414 274; in these processes, it is also possible to use the hemiacetals or acetals of the dialdehydes. As catalyst, use is made of a monolithic catalyst comprising a noble metal on a metal support coated with aluminum/silicon oxide. A disadvantage of these processes is that a two-stage reaction starting from alkoxydihydropyrans, namely acid hydrolysis and subsequent hydrogenation, is necessary.

There have therefore been attempts to convert alkoxydihydropyran directly into pentanediol in a single-stage process. DE-A 1 003 704 and U.S. Pat. No. 2,546,019 describe processes in which pentanediol is obtained by single-stage reaction of alkoxydihydropyran with water and hydrogen in the presence of a catalyst. Hydrogenation catalysts which are said to be able to be used are metals such as Pt, Pd, Au, Ag, Zn, V, W, Co, Ni, Ru, Rh, Mn, Cr, Mo, Ir, Os, Pb, their alloys and also their oxides and sulfides. As preferred hydrogenation catalysts, mention is made of pyrophoric metal hydrogenation catalysts comprising nickel, cobalt and iron. These hydrogenation catalysts, which are known as Raney catalysts, can be dispersed as finely divided powders in the reaction solution or can also be used as fixed-bed catalysts in the form of relatively large particles. A further possibility mentioned is to apply the metal catalyst to a support material such as pumice or kieselguhr. Disadvantages of the finely divided Raney catalysts are their pyrophoric properties, which mean that the powders have to be handled under inert gas, and also their toxicity. Reactions using finely divided Raney catalysts are predominantly carried out batchwise, and the suspension has to be filtered after the reaction. Carrying out these reactions continuously is relatively difficult, since continuously the reaction mixture has to be filtered and the catalyst retained on the filter has to be returned to the reactor. Furthermore, the production of Raney catalysts, which are suitable as fixed-bed catalysts, is technically complicated.

It is an object of the present invention to provide a single-stage process for preparing pentanediols from alkoxydihydropyrans, which makes do without the use of Raney catalysts.

We have found that this object is achieved by a process for preparing 1,5-pentanediols of the formula (I)

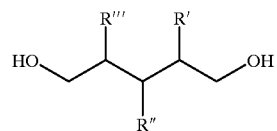

by single-stage reaction of alkoxydihydropyrans of the formula (II)

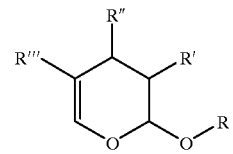

where, in the formulae (I) and (II),

R, R', R", R''' can be identical or different and are each hydrogen or a linear or branched saturated hydrocarbon radical having from 1 to 20 carbon atoms in which the hydrocarbon chain may contain O, S and N as heteroatoms and which may be monosubstituted or polysubstituted by hydroxy, thiol or amino groups or halogens, with water and hydrogen in the presence of a catalyst comprising oxides of nickel, zirconium and copper.

The catalyst used according to the present invention comprises oxides of nickel, zirconium and copper. The catalyst may further comprise molybdenum oxide. The catalyst used according to the present invention preferably comprises from 20 to 75% by weight, particularly preferably from 30 to 70% by weight, very particularly preferably from 40 to 60% by weight and especially from 35 to 55% by weight, of nickel oxide, preferably from 10 to 75% by weight, particularly preferably from 10 to 60% by weight, very particularly preferably from 15 to 50% by weight and especially from 25 to 45% by weight, of zirconium dioxide and preferably from 5 to 50% by weight, particularly preferably from 5 to 40% by weight, very particularly preferably from 10 to 35% by weight and especially from 10 to 20% by weight, of copper oxide. The catalyst may further comprise up to 5% by weight, for example from 0.1 to 5% by weight, of molybdenum oxide. The proportions by weight indicated are in each case based on the oxidic, unreduced catalyst and add up to 100% by weight.

In one embodiment, the catalyst used according to the present invention comprises nickel oxide, zirconium dioxide and copper oxide and no molybdenum oxide. In a further embodiment, the catalyst used according to the present invention further comprises 0.1–5% by weight of molybdenum oxide. The catalysts according to the present invention preferably comprise only the metals nickel, zirconium, copper and, if desired, molybdenum and any further metals only in traces, for example in amounts of <1 mol %, preferably <0.1 mol %, based on the total metal content. Preference is thus given to catalysts which consist essentially of the abovementioned metal oxides in the amounts specified above.

In general, the catalysts used according to the present invention are used in the form of unsupported catalysts. For the purposes of the present invention, the term "unsupported catalyst" refers to a catalyst which, in contrast to a supported catalyst, consists only of catalytically active composition. Unsupported catalysts can be used by introducing the catalytically active composition milled to a powder into the reaction vessel or by converting the catalytically active composition into shaped catalyst bodies, for example spheres, cylinders, rings or spirals, by milling, mixing with shaping aids, shaping and heat treatment and installing these in the reactor.

In general, precipitation methods are employed for preparing the catalysts used according to the present invention. Thus, for example, they can be obtained by coprecipitation of the nickel and copper components from an aqueous salt solution containing these elements by means of mineral bases in the presence of a slurry of a sparingly soluble, oxygen-containing zirconium compound and subsequent washing, drying and calcination of the precipitate obtained. Sparingly soluble, oxygen-containing zirconium compounds which can be used are, for example, zirconium dioxide and hydrated zirconium oxide. Molybdenum can be added before drying as ammonium heptamolybdate.

The catalysts used according to the present invention can be obtained by coprecipitation of the nickel and copper components by adding an aqueous mineral base, in particular an alkali metal base such as sodium carbonate, sodium hydroxide, potassium carbonate or potassium hydroxide, while stirring to a hot aqueous salt solution containing copper and nickel until precipitation is complete. The precipitates obtained in these precipitation reactions are generally chemically nonuniform and comprise, inter alia, mixtures of oxides, hydrated oxides, hydroxides, carbonates and insoluble basic salts of the metals used. It may be found to be advantageous to age the precipitates to improve their filterability.

The catalyst used according to the present invention is preferably prepared by precipitating salts of the metals nickel, copper and zirconium in aqueous solution at from 30 to 90° C. and a pH of from 5 to 9, filtering the suspension, drying the filter cake and heating it at from 300 to 700° C. If desired, molybdenum is added as ammonium heptamolybdate before drying. The precipitation is carried out by mixing an aqueous solution of salts, e.g. the nitrates, sulfates or acetates, of the metals nickel, copper and zirconium, with an aqueous solution of alkali metal carbonate. The amounts of the metal salts are calculated so that the catalyst composition has the specified composition after heat treatment.

In a further, preferred variant of the preparation of the catalyst used according to the present invention, part of the water-soluble zirconium salt, for example a proportion of up to 50% by weight based on the zirconium used, is replaced by solid zirconium dioxide which is added to the aqueous metal salt solution prior to precipitation or is placed in the reaction vessel.

In the preparation of the catalyst used according to the present invention, the aqueous solution of the metal salts is, for example, mixed simultaneously while stirring with an aqueous alkali metal carbonate solution, preferably sodium carbonate solution, resulting in precipitation of the metals in the form of a mixture of metal hydroxides and metal carbonates. The metal salt content of the metal salt solution is preferably from 30 to 40% by weight. The aqueous alkali metal carbonate solution preferably has a concentration of from 15 to 20% by weight.

The suspension obtained is filtered and washed with water until no more anions can be detected. It is subsequently dried at from 120 to 200° C. in a drying oven or in a spray dryer. The molybdenum is, if used, added as ammonium heptamolybdate to the moist filter cake. The dried filter cake is heat treated at from 350 to 700° C., preferably from 400 to 600° C. The catalyst composition obtained in this way can be tableted or extruded prior to use. For example, the catalyst composition is mixed with a tableting aid, preferably graphite, and pressed to give pellets having dimensions of 6×3 mm. The pellets produced in this way are heat treated at from 300 to 700° C., preferably from 400 to 600° C. The pellets obtained in this way generally have a mean density of from 1500 to 1900 g/l, a porosity (determined by water absorption) of from 0.2 to 0.4 ml/g and a hardness of from 3000 to 4000 N/cm$^2$. The catalyst obtainable in this way is generally subjected before use in the process of the present invention to a reductive treatment with hydrogen at from 200 to 350° C., preferably from 230 to 280° C., for a period of, for example, from 20 to 40 hours at a hydrogen pressure of generally from 1 to 300 bar, preferably from 100 to 150 bar.

The catalysts used according to the present invention can also be prepared by peptizing pulverulent mixtures of hydroxides, carbonates, oxides and/or salts of nickel, zirconium, copper and, if desired, molybdenum with water and subsequently extruding and heat treating the compositions obtained in this way.

The 1,5-pentanediols of the formula (I) are obtained by reaction of alkoxydihydropyrans of the formula (II) according to the reaction equation below:

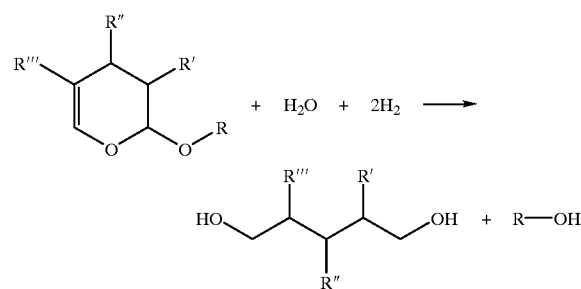

In the formulae (I) and (II), R, R', R", R'" can be identical or different and are each hydrogen or a linear or branched saturated hydrocarbon radical. Preferred hydrocarbon radicals are $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and 2-ethylhexyl; the $C_1$–$C_4$-alkyl radicals mentioned are particularly preferred.

In the hydrocarbon radicals, O, S and N may be present as heteroatoms in the hydrocarbon chain. Examples of such radicals are $C_2$–$C_{20}$-alkoxyalkyl, preferably $C_2$–$C8$-alkoxyalkyl, particularly preferably $C_2$–$C_4$-alkoxy-alkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, $C_2$–$C_{20}$-alkylthioalkyl such as the alkylthioalkyl radicals corresponding to the abovementioned alkoxyalkyl radicals, $C_3$–$C_{20}$-dialkyl-aminoalkyl, preferably $C_3$–$C_{10}$-dialkyl-aminoalkyl such as dimethylamino-methyl, diethylaminoethyl, di-n-propylaminoethyl and diisopropylaminoethyl, and $C_2$–$C_{20}$-alkylaminoalkyl, preferably $C_2$–$C_8$-alkylaminoalkyl such as methylamino-methyl, methylaminoethyl, ethylaminomethyl, ethylaminoethyl and isopropyl-aminoethyl.

The hydrocarbon radicals mentioned can be monosubstituted or polysubstituted by hydroxy, thio or amino groups or halogens.

Particular preference is given to using alkoxydihydropyrans of the formula (IIa)

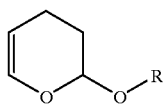

(IIa)

where R is linear or branched $C_1$–$C_4$-alkyl.

In particular, use is made of the following alkoxydihydropyrans:
2-methoxy-2,3-dihydro-4H-pyran, 2-ethoxy-2,3-dihydro-4H-pyran, 2-propoxy-2,3-dihydro-4H-pyran, 2-butoxy-2,3-dihydro-4H-pyran and 2-isobutoxy-2,3-dihydro-4H-pyran.

The process of the present invention is preferably carried out at from 50 to 250° C., particularly preferably from 100 to 200° C., and a pressure of preferably from 100 to 300 bar absolute, particularly preferably from 50 to 220 bar absolute. The pressure is maintained by addition of hydrogen. The process can be carried out continuously or batchwise and in both cases hydrogen can be circulated. The reactor can be operated in suspension or fixed-bed mode. Water and the alkoxydihydropyran are introduced in liquid form into the reactor, preferably in a molar ratio of water to alkoxydihydropyran of from 1.5:1 to 10:1, particularly preferably from 3:1 to 8:1, based on the freshly introduced feed. In general, from 0.1 to 5.0 kg, preferably from 0.3 to 1.5 kg, of alkoxydihydropyran is reacted per kilogram of catalyst per hour.

The process of the present invention is preferably carried out continuously, and the reactor is preferably operated in the fixed-bed mode. The reactor can be operated either in the upflow mode or in the downflow mode, i.e. the liquid reactor feed can be passed through the catalyst bed either from the top downward or from the bottom upward. The hydrogen can be passed through the reactor either in cocurrent or in countercurrent to the liquid feed.

In steady-state operation of the reactor in a continuous process, part of the liquid reactor product is preferably recirculated to the reactor, with particular preference being given to recirculating from 2 to 10 kg of the liquid reactor product to the reactor for every kilogram of fresh alkoxydihydropyran fed in.

The reactor is preferably followed by a separator in which the reactor product is depressurized and hydrogen gas and liquid are separated from one another. In general, the major part of the hydrogen, preferably from 70 to 95% by volume is recirculated to the reactor. The liquid reactor product taken off can be worked up in a manner known per se. It is preferably subjected to a two-stage rectification in which water and the alcohol formed, for example methanol, are separated off in the first stage and pure 1,5-pentanediol is isolated in the second stage under reduced pressure.

The invention is illustrated by the following examples.

EXAMPLES

Preparation of the Catalysts

The catalysts A and B used in the process of the present invention are prepared by the method described in EP-A 0 394 842.
Catalyst A:

Nickel nitrate, copper nitrate and zirconium acetate are dissolved in distilled water to give a solution having a calculated NiO content of 4.48% by weight, a CuO content of 1.52% by weight and a $ZrO_2$ content of 2.8% by weight. To carry out the precipitation, a constant stream of a 20% strength aqueous carbonate solution is added at 70° C. to the above solution in a stirred vessel at such a rate that the pH of the mixture is maintained at 7.0 during the precipitation. The suspension obtained is filtered and the filter cake is washed with distilled water until the filtrate has an electrical conductivity of 20 $\mu$S. An amount of ammonium heptamolybdate corresponding to 30 g of $MoO_3$ per kg of NiO is subsequently worked into the moist filter cake and the filter cake is dried at 150° C. The resulting hydroxide/carbonate mixture is subsequently heated at 500° C. for 4 hours. The catalyst composition obtained consists of 50% by weight of NiO, 17% by weight of CuO, 1.5% by weight of $MoO_3$ and 31.5% by weight of $ZrO_2$. The catalyst powder is mixed with 3% by weight of graphite and pressed to form pellets having a diameter of 6 mm and a thickness of 3 mm. The pellets have a porosity of 0.30 ml/g and a hardness of 3500 $N/cm^2$.
Catalyst B:

The procedure for the preparation of catalyst A is repeated, except that no ammonium heptamolybdate is added. The resulting catalyst consists of 51% by weight of NiO, 17% by weight of CuO and 32% by weight of $ZrO_2$. The catalyst powder is mixed with graphite and pressed to form pellets as described above.

Preparation of 1,5-pentanediol

Comparative Example C1 (in accordance with U.S. Pat. No. 2,546,019)

144.82 g (=1.269 mol) of 2-methoxy-2,3-dihydro-4H-pyran (MOP), 45.76 g (=2.54 mol) of water and 9.4 g of Raney nickel were placed in a stirring autoclave having a gross capacity of 300 ml and the autoclave was pressurized with 100 bar of hydrogen. The reactor was heated while stirring to 150° C. and held at this temperature for 4 hours. The reactor was subsequently cooled and depressurized to atmospheric pressure. The contents of the reactor were filtered, giving 190 g of filtrate. The organic constituents of the filtrate were determined by GC analysis and the water content was determined by Karl-Fischer titration. A pentanediol concentration of 48.1% by weight was found, which corresponds to a total amount of 91.7 g of pentanediol (=0.88 mol). The yield was thus 69 mol %, based on MOP used. The space-time yield was 120 g/(l×h).

Examples 1 and 2

The procedure of the comparative example was repeated, except that the catalysts A and B were used in place of Raney nickel. In each case, 9.4 g of finely milled catalyst were used.

The results are summarized in the following table.

| Example No. | C1 | 1 | 2 |
|---|---|---|---|
| Catalyst | Raney Ni | Cat. A | Cat. B |
| Catalyst [g] | 9.4 | 9.4 | 9.4 |
| Conversion based on MOP [%] | 99.95 | 99.97 | 100.00 |
| PDO in product [% by weight] | 48.15 | 57.3 | 53.2 |
| Yield of pentanediol [g] | 91.7 | 109.3 | 101.3 |
| Space-time yield [g/(l*h)] | 120.2 | 143.3 | 132.9 |
| Selectivity based on MOP [mol/mol] | 69.4% | 82.7% | 76.7% |

As the table shows, the catalysts according to the present invention give a significantly higher selectivity of conversion to 1,5-pentanediol and a significantly higher space-time yield than does Raney nickel.

Continuous Reaction

Example 3

A continuous reaction was carried out using a high-pressure reactor having an internal diameter of 30 mm and a total height of 2000 mm. The reactor is provided with a thermocouple having a diameter of 12 mm arranged axially. The lower part of the reactor is packed with 500 ml of stainless steel Pall rings, above which 500 ml (=760 g) of catalyst A in pellet form and, as uppermost bed, 250 ml of Pall rings are installed. At the bottom of the reactor, 250 g/h of 2-methoxy-2,3-dihydro-4H-pyran (MOP), 250 g/h of water and 500 g/h of the liquid reaction product are fed in via separate lines. Hydrogen was introduced at the bottom of the reactor, with the amount of hydrogen being regulated so that the off-gas flow was constant at 100 standard l/h. The reactor was operated in the upflow mode at 150° C. under a hydrogen pressure of 200 bar absolute. The reactor product was cooled and depressurized to atmospheric pressure, and the part of the reactor product which was not recirculated was taken off as crude product.

The crude product comprised 42% by weight of water, 1.6% by weight of tetrahydropyran, 8.7% by weight of methanol, 47.5% by weight of 1,5-pentanediol and 0.2% by weight of further organic by-products. The conversion based on MOP was 100%, and the yield of 1,5-pentanediol was 96.4% based on MOP used.

The crude product (500 g) was subjected to a simple distillation in which it was firstly dewatered under atmospheric pressure to give 259 g of distillate (water and methanol) and subsequently distilled at 30 mbar, giving 220.5 g of pentanediol having a purity of 99% by weight. The distillation yield was thus 92.8% by weight of the 1,5-pentanediol present in the crude product; the total yield based on MOP used was 89.5%. The space-time yield for the 1,5-pentanediol present in the crude product based on the catalyst volume was 475 g/(l×h).

We claim:

1. A process for preparing 1,5-pentanediols of the formula (I)

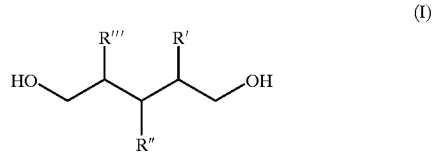

(I)

by single-stage reaction of alkoxydihydropyrans of the formula (II)

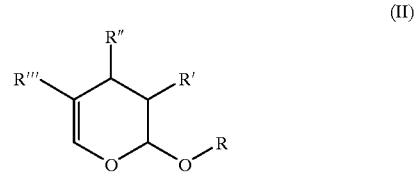

(II)

where, in the formulae (I) and (II),

R, R', R", R'" can be identical or different and are each hydrogen or a linear or branched saturated hydrocarbon radical having from 1 to 20 carbon atoms in which the hydrocarbon chain may contain O, S and N as heteroatoms and which may be monosubstituted or polysubstituted by hydroxy, thiol or amino groups or halogens, with water and hydrogen in the presence of a catalyst comprising oxides of nickel, zirconium and copper.

2. A process as claimed in claim 1, wherein the catalyst comprises from 20 to 75% by weight of NiO, from 10 to 75% by weight of $ZrO_2$, from 5 to 50% by weight of CuO and from 0 to 5% by weight of $MoO_3$, where the sum of the oxides specified is 100% by weight.

3. A process as claimed in claim 1, wherein alkoxydihydropyrans of the formula (IIa)

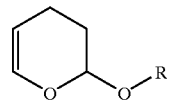

(IIa)

where

R is linear or branched $C_1$–$C_4$-alkyl, are used.

4. A process as claimed in claim 1, wherein the reaction is carried out at from 50 to 250° C. and a pressure of from 10 to 300 bar absolute.

5. A process as claimed in claim 1, wherein water and alkoxydihydropyran are present in the fresh feed to a reactor in a molar ratio of water to alkoxydihydropyran of from 1.5:1 to 10:1.

6. A process as claimed in claim 1, wherein the reaction is carried out continuously in a reactor in suspension or fixed-bed mode at a throughput over the catalyst of from 0.1 to 5.0 kg of alkoxydihydropyran/($kg_{catalyst}$×h).

7. A process as claimed in claim 6, wherein, in steady-state operation of the reactor, part of the liquid reactor product is recirculated to the reactor in an amount of from 2 to 10 kg for every kilogram of fresh alkoxydihydropyran fed in.

8. A process as claimed in claim 6, wherein the reaction is carried out in the fixed-bed mode and the catalyst is present as a loose bed of shaped catalyst bodies through which the liquid reactor feed flows from the top downward or from the bottom upward, with the hydrogen being able to be passed through in cocurrent or countercurrent.

* * * * *

UNITED STATES PATENT AND TRADEMARK OFFICE
CERTIFICATE OF CORRECTION

PATENT NO. : 6,403,845 B1
DATED : June 11, 2002
INVENTOR(S) : Pfeffinger et al.

It is certified that error appears in the above-identified patent and that said Letters Patent is hereby corrected as shown below:

<u>Title page,</u>
Item [57], ABSTRACT, before the formula (I), insert the following:
-- 1,5-Pentanediols of the formula (I) --.

Signed and Sealed this

Eighth Day of October, 2002

Attest:

Attesting Officer

JAMES E. ROGAN
*Director of the United States Patent and Trademark Office*